Figure 4:
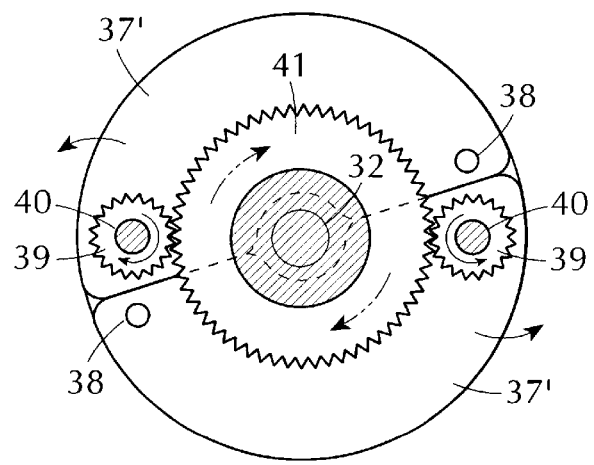
Figure 5:
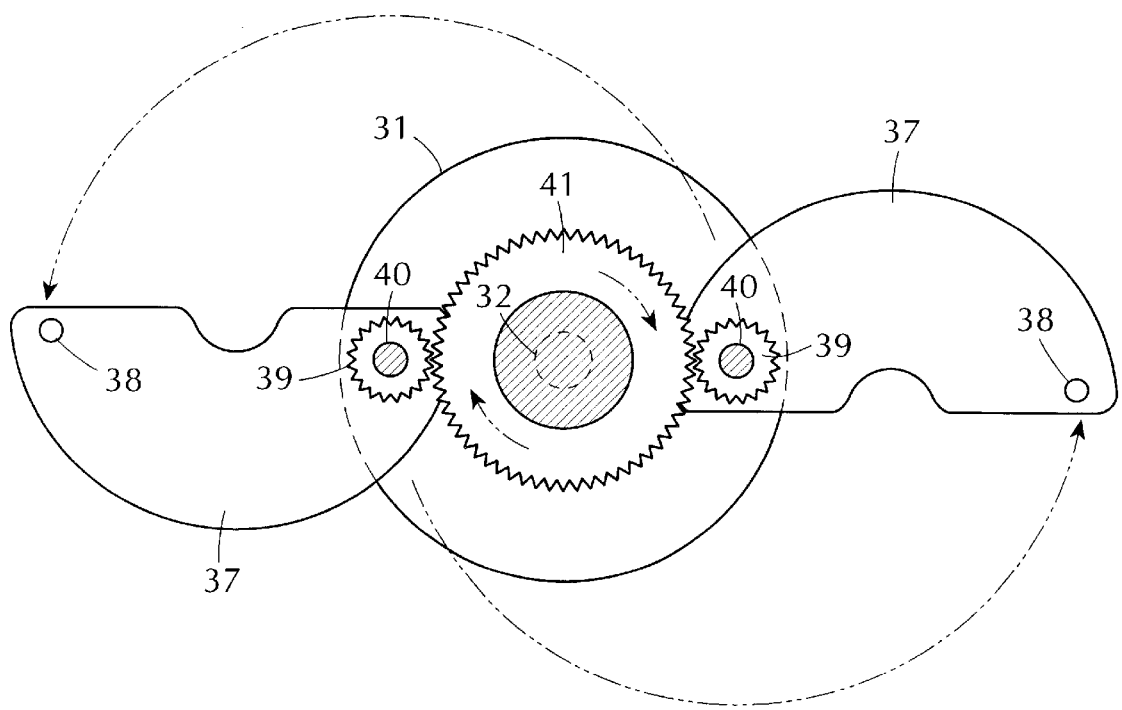

United States Patent [19]
Greenstein

[11] Patent Number: 5,964,773
[45] Date of Patent: Oct. 12, 1999

[54] LAPARASCOPIC SUTURING DEVICE AND SUTURE NEEDLES

[75] Inventor: Robert J. Greenstein, Tenafly, N.J.

[73] Assignee: Automated Medical Products, Inc., Edison, N.J.

[21] Appl. No.: 08/882,812

[22] Filed: Jun. 26, 1997

Related U.S. Application Data

[63] Continuation of application No. 08/388,690, Feb. 15, 1995.

[51] Int. Cl.[6] ..................................................... A61B 17/04

[52] U.S. Cl. ........................... 606/148; 606/144; 606/147

[58] Field of Search ..................................... 606/222–227, 606/148, 144, 145, 147, 139; 112/169, 80.03, 222; 289/16; 223/102–104; 163/5

[56] References Cited

U.S. PATENT DOCUMENTS

| | | | |
|---|---|---|---|
| 4,672,734 | 6/1987 | Kawada et al. | 606/223 |
| 5,374,275 | 12/1994 | Bradley et al. | 606/148 |
| 5,403,329 | 4/1995 | Hinchcliffe | 606/144 |
| 5,437,680 | 8/1995 | Yoon | 606/223 |

FOREIGN PATENT DOCUMENTS

| | | | |
|---|---|---|---|
| 4210724 | 7/1993 | Germany | 606/144 |

*Primary Examiner*—Michael Buiz
*Assistant Examiner*—Tina T. D. Pham
*Attorney, Agent, or Firm*—Blank Rome Comisky & McCauley LLP

[57] ABSTRACT

A surgical suturing tool comprising a suture needle holder and suture needle is disclosed. The needle includes a groove in its sidewall which leads to a blind hole to receive one end of a suture which is secured therein by swedging.

10 Claims, 5 Drawing Sheets

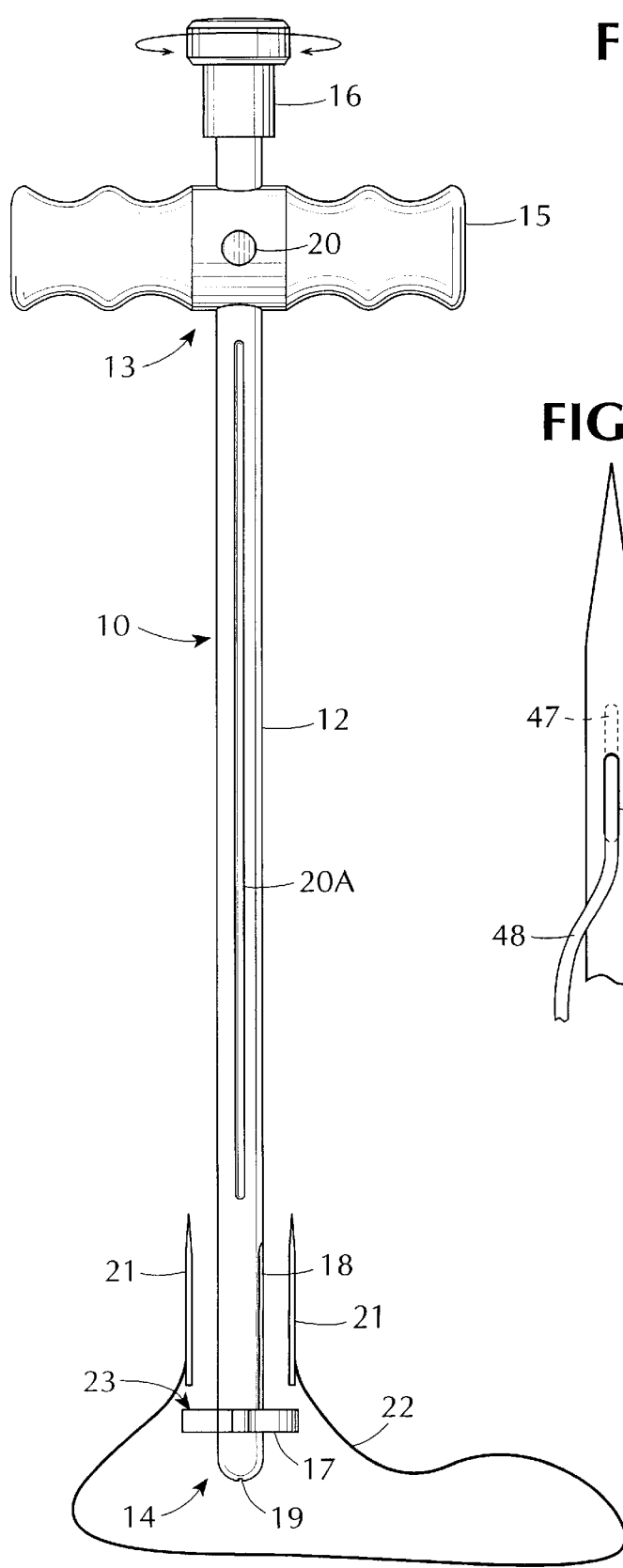
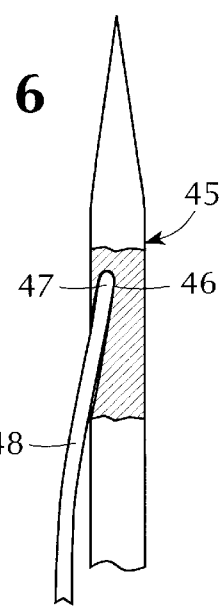
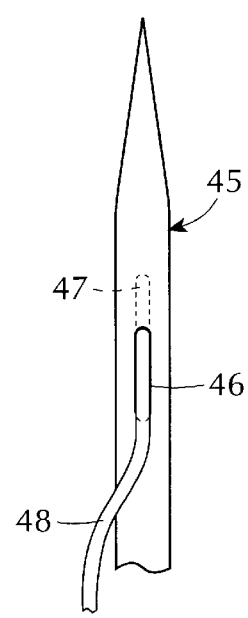
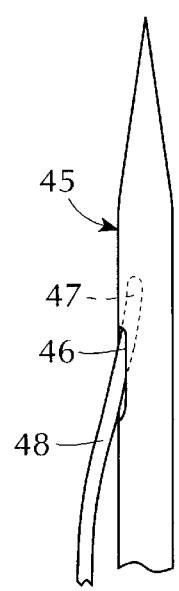
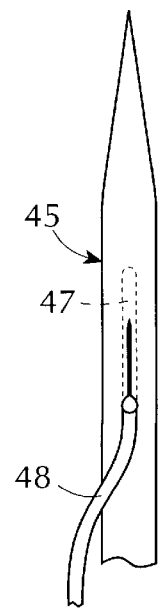

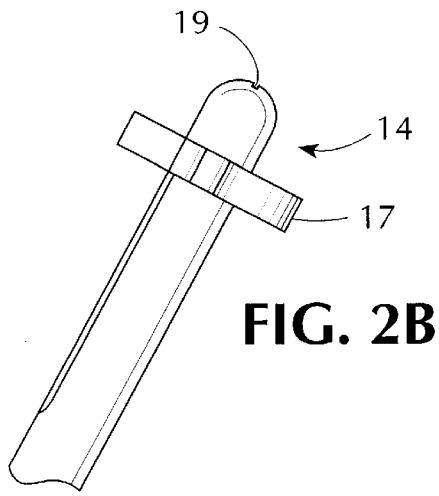
FIG. 2B
FIG. 2A
FIG. 2C
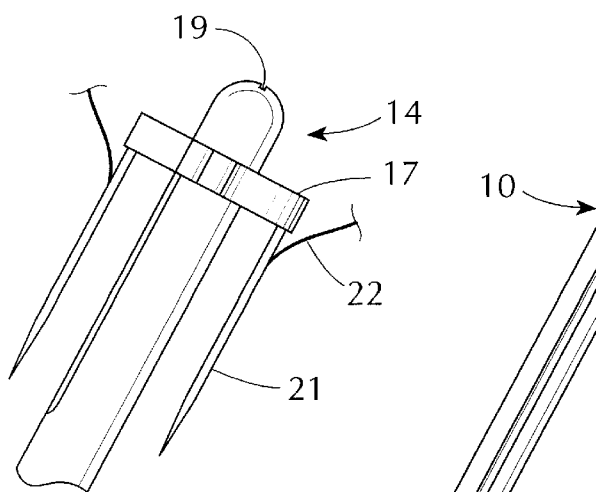
FIG. 2D
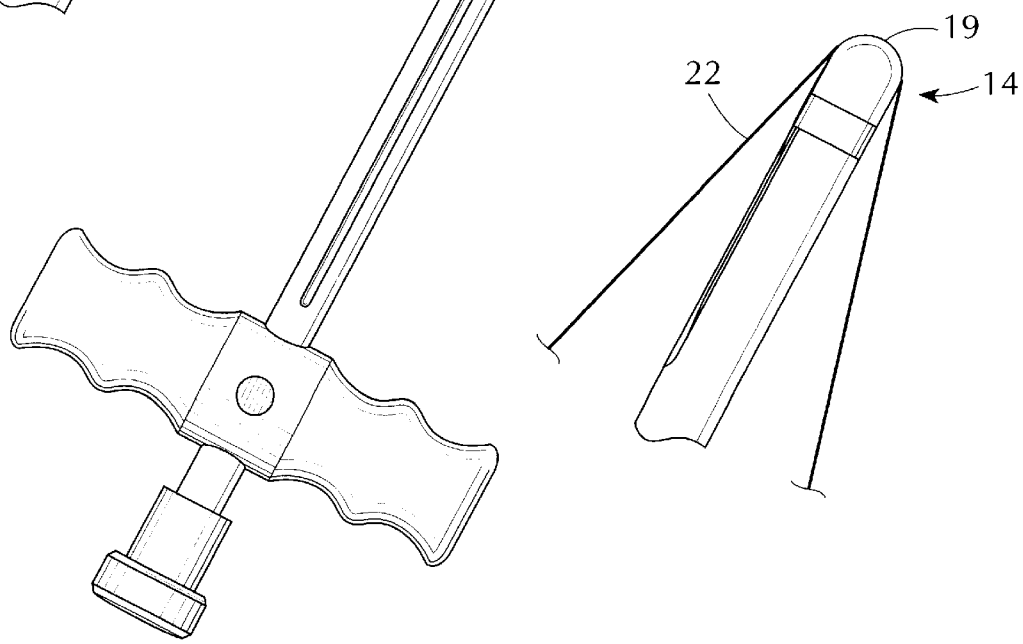

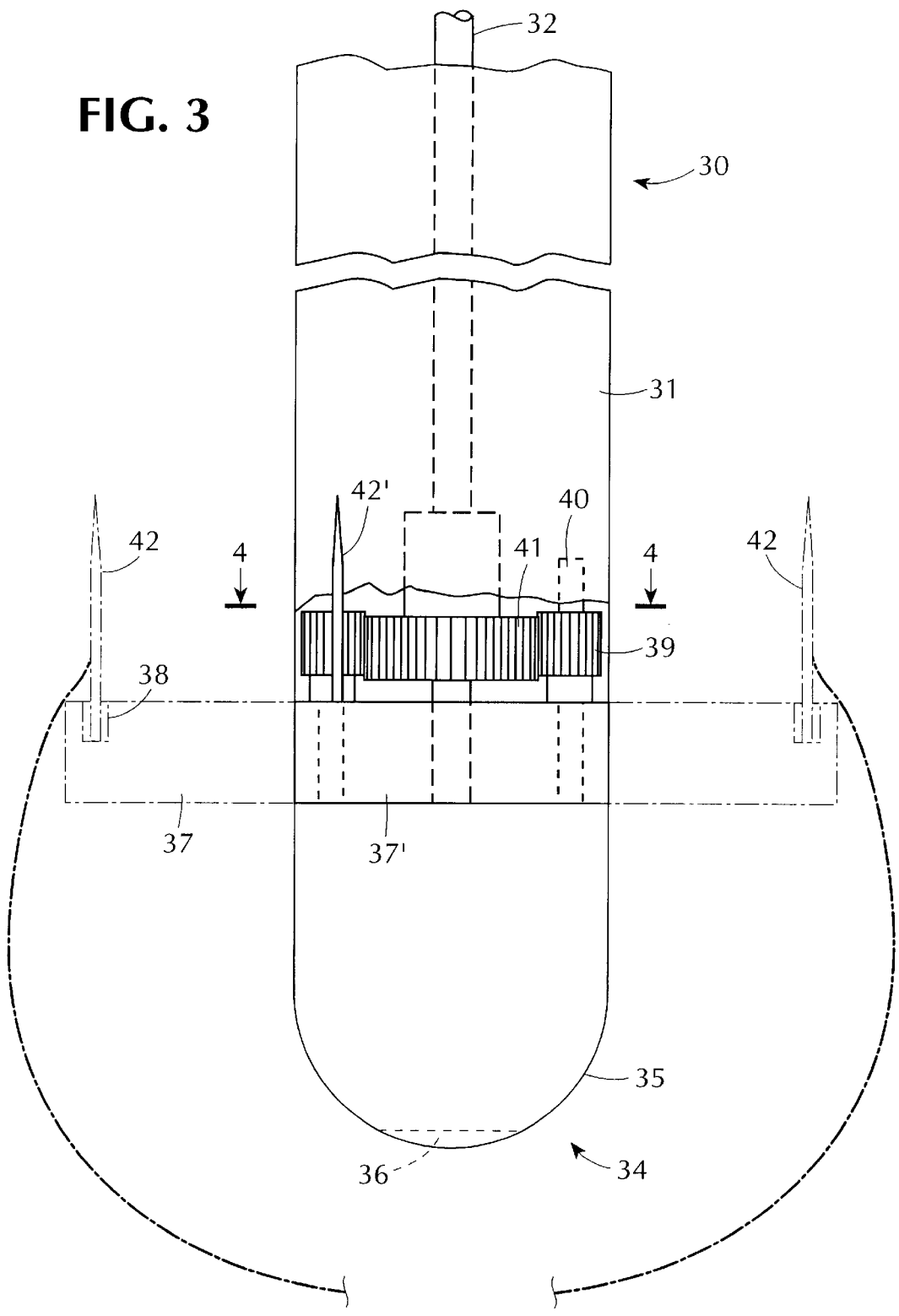

LAPARASCOPIC SUTURING DEVICE AND SUTURE NEEDLES

This is a continuation of co-pending application Ser. No. 08/388.690, filed on Feb. 15, 1995.

FIELD OF THE INVENTION

This invention is in the field of laparascopic suturing devices and suturing needles used therewith, and surgical techniques for closure of trochar holes and other openings and wounds particularly in abdominal surgery.

BACKGROUND OF THE INVENTION

In laparascopic surgery a known device called Deep Suture is a needle holder made by REMA® Medizintechnik GmbH of Germany, D-7201 Durbheim-Tuttlingen, In Breiten 10 Germany. It is believed that a German patent corresponding to this device is DE 42 10 724 C1, a copy of which in German is attached hereto as Appendix A and incorporated herein by reference.

While this device has various inherently good features, a number of significant improvements have been developed as disclosed in this application. The prior device, in summary, has a central shaft with proximal and distal ends. Extending through the shaft is a rotatable rod having a control handle at the proximal end and a drive gear at the distal end. A pair of driven gears are positioned at the periphery of the drive gear at opposite sides thereof, each driven gear coupled to an arm or wing that pivots radially outward from the shaft when the control handle is turned. Each wing includes a recess or blind hole for receiving the proximal end of a suture needle. In operation a single strand of suture material has its ends threaded through the eye of each of the needles, the suture then extending as a double strand from each needle. The proximal ends of the needles are then inserted in the wings, and the wings are pivoted to their retracted position whereby they and the needles are radially inward of the outer cylindrical boundary established by the central shaft. To facilitate this an axial groove is provided in the shaft into which each needle can move. The device, with wings retracted, is inserted down into the opening in the abdominal wall produced by a trocar. During insertion the suture is dragged down.

When adequately inserted downward the wings are pivoted to open position exposing the needles now pointing upward. The shaft is withdrawn until the needles pierce the wall and protrude out of the wall. These needles are engaged individually by a clamp, forceps or a needle holder or by a clamping device movable axially on the shaft and drawn through the tissue, pulling the suture until it forms a loop beneath the opening. The wings, now empty of needles, are pivoted closed, and the shaft is extracted from the opening. The needles are cut off the suture ends and the suture is tied.

The improvements in this device are described below.

SUMMARY OF THE NEW INVENTION

During the procedure described above the needles may become dislodged and separate from the wings. The new invention provides in combination an improved needle and improved insertion device with a groove in the distal end of the central shaft. Each needle has a groove in its side wall to receive one end of the suture which is secured therein, as by swedging. The grooves in the needles are preferably inclined downward. The suture exits the groove oriented angularly downward toward the proximal end of the needle which is also in the direction toward the wing and toward the distal end of the central shaft.

In operation the needles are situated with their proximal ends in the blind holes in the wings and the suture line extending from each needle is drawn downward to lie in the groove. The remainder of the suture extends upward toward the handle and is held and guided by the operator. By pulling upward on said remainder of the suture (which extends as a continuous strand between the needles), the needles are pulled downward to remain securely seated in the wings. The needles are urged downward because the groove through which the suture is pulled lies further below the wings than the lower ends of the needles.

BRIEF DESCRIPTION OF THE DRAWINGS

FIG. 1 is an exploded elevation of the new device and the new needles.

FIG. 2A is an elevation of the new device, and

FIGS. 2B, 2C, and 2D are fragmentary elevations of the distal end of the device at different stages.

FIG. 3 is a fragmentary elevation partially cut away showing the drive mechanism.

FIG. 4 is a sectional view taken along line 4—4 in FIG. 3, with the wings closed.

FIG. 5 is a sectional view similar to FIG. 4 with the wings open.

FIG. 6 is fragmentary section view of the new needle

FIGS. 7 and 8 are fragmentary front and side views of the needle of FIG. 6.

FIG. 9 is a fragmentary front view shown schematically of a needle with a groove swedged closed capturing the end of a suture.

FIG. 10 is a schematic view of the new device when inserted and the wings are open.

FIG. 11 is a schematic view similar to FIG. 10.

DETAILED DESCRIPTION OF THE PREFERRED EMBODIMENT

FIG. 1 shows a first embodiment 10 of the new suturing device including the central shaft 12 with proximal end 13 and distal end 14. At the proximal end is handle 15 and control knob 16. At the distal end are wings 17, grooves or channels 18 corresponding in length to the needles to receive the needles and guide notch 19. In handle 15 is a cleaning port 20. Along the length of shaft 12 is a depth gage 21. Also shown are needles 21 and suture 22 positioned for insertion into blind holes 23 in the wings.

FIG. 2A shows device 10 oriented upside down relative to FIG. 1, with the wings 17 in fully closed condition; FIG. 2B shows the distal end 19 of the device with the wings partially open; FIG. 2C shows the distal end with the wings fully open; and FIG. 2D shows the distal end with the suture 22 lying in groove 19.

FIGS. 3 and 4 show a typical drive mechanism 30 for the new device, the components thereof corresponding generally to the device of FIGS. 1 and 2A. In FIGS. 3 and 4 the shaft 31 has a distal end 34 with the suture guide groove 36 shown in dotted line. Through shaft 31 is drive rod 32 coupled to drive gear 41 which is further coupled to driven gears 39, each of which is secured to a wing 37. Needles 42 are removably situated in blind holes 38 in the wings. The wings in closed position are designated by 37' in FIG. 3 along with needles 42' in closed position. Driven gears 39 revolve on pivots 40.

Rotation of control knob (not shown) rotates rod 32 and drive gear 41. This causes driven gears 37 to pivot radially outward carrying needles 42 to their open position.

FIGS. 6–16 show a new needle 45 with its groove 46 and end 47 of suture 48 swedged therein. The groove 46 may extend to various depths or as a blind hole for receiving the end of the suture. The groove and/or hole may be formed by cutting, lancing, forging or other techniques.

Securing the suture end to the needle is thereafter done by swedging, peening or otherwise deforming the metal of the needle adjacent the suture to achieve a clamping action on the suture. Other adhering techniques may be used, but ideally the suture extends from the needle with substantially little added thickness or effective diameter of the needle.

The groove is oriented to lead the suture out of the side surface of the needle at an angle downward toward the proximal end of the needle, opposite the point. The angle of exit is preferably small, as between 1° and 20°. The exit of the groove or the point of exit from the side surface of the needle is near the proximal end or closer to that end than the point.

Thus, when the needle is seated in the hole in a wing, pulling on the suture will apply a force tending to keep the needle well-seated down in the hole in the wing, particularly during the suturing procedure.

The use of a groove and/or blind hole allows the suture to exit at the downward angle and thus avoid the double thickness of suture if the traditional suture "threaded" through the eye at a general 90° angle therefrom which creates highly undesirable drag as the needle is pulled through the abdominal wall.

The new device and new needles herein described may be used for closing trochar holes not only in abdominal walls, but in thoracic walls and other deep or difficult to reach areas.

A further feature of this invention is a cleaning port and Luer fitting situated in the handle. When opened the port allows high pressure cleaning solution from a syringe or other source to flow down the central aperture containing the drive rod and to the gears and wings.

Figure 10:
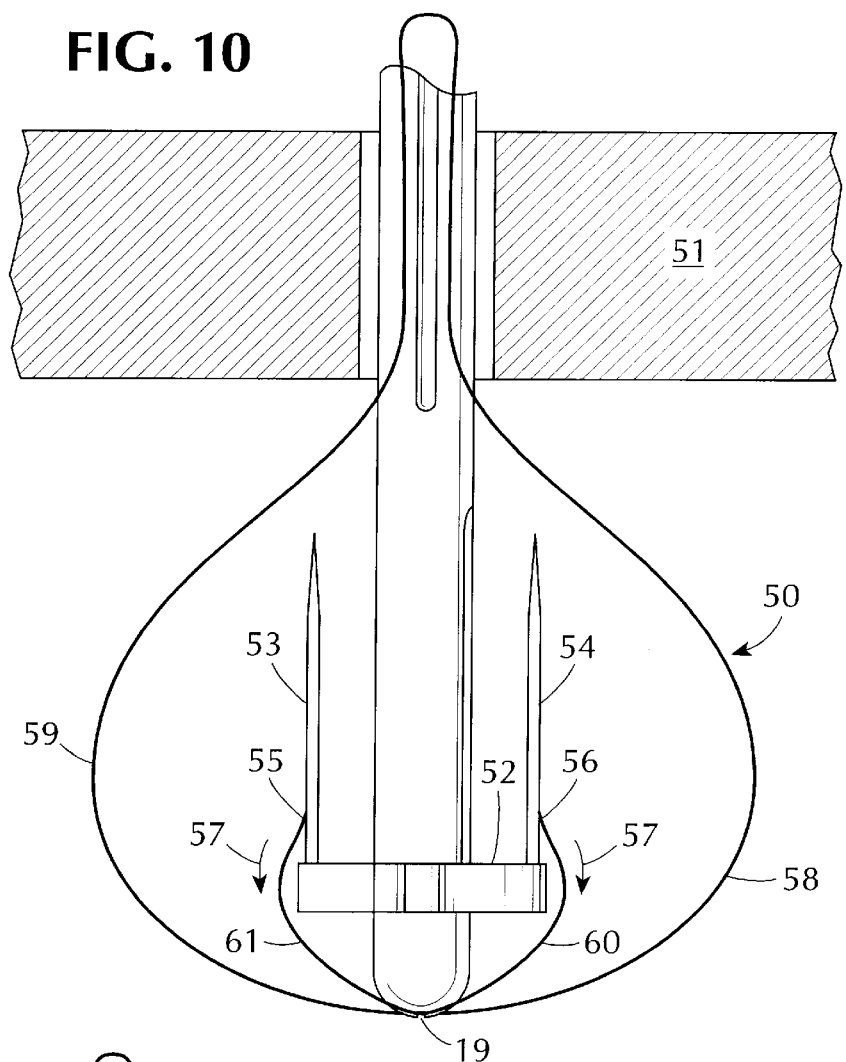
Figure 11:
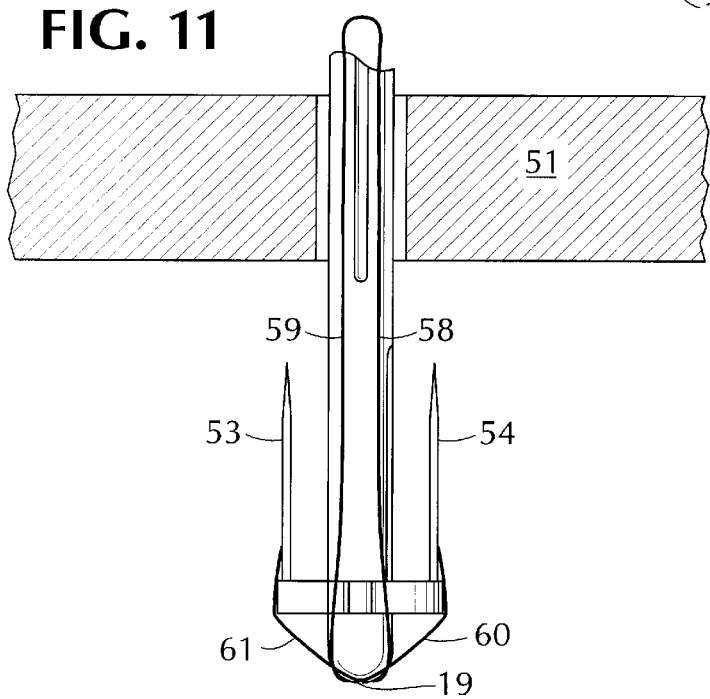

FIG. 10 shows schematically the suturing device 50 inserted through he abdominal wall 51, with the wings 52 open and needles 53 and 54 positioned for penetration of the wall. Suture ends 55 and 56 extend from needles 53 and 54 respectively in a downward direction of arrows 57 through guide notch 19 and thence upward. In practice the segments 58, 59 of the suture as seen in FIG. 11 are pulled together and upward along the shaft to be held by the surgeon's finger in order to maintain secure downward tension on segments 60 and 61 and thus to apply constant downward seating force on the needles in the wings.

The insertion device is made of stainless steel or equivalent, with a plastic handle or as available from REMA® referred to above. Suture needles are made pursuant to standard commercial practice as typically made by Surgical Specialties Corp., P.O. Box 310, Reading, Pa. 19607, also called Sharpoint®, one embodiment being 0.0505 diameter, taper point 1–0 polypropylene or catgut suture 20" double armed. Teaching for needles and sutures may be seen in U.S. Pat. No. 3,799,169 which is incorporated herein by reference and a copy is attached hereto as Appendix B. For the invention herein a suture length of 40–100 cm would be used, one specific preference being 60 cm. Also with this invention needle length would be in the range of about 3–10 cm. A great variety of commercially available suture material may be selected as determined by the surgeon and the procedure.

Various other structures and arrangements besides those depicted herein are possible within the spirit and scope of this invention and as set forth in the claims appended hereto.

I claim:

1. A surgical suturing tool, comprising:
    a) a suture needle comprising an elongated essentially straight shaft which traverses an essentially linear path of travel and having a first end tapered to a point, a second end, and a medial portion between the first end and second end, said medial portion having an axially aligned groove leading to a blind hole into which a surgical suture can be fixedly secured, said groove oriented to lead the surgical suture out of a side surface of the suture needle at an angle downward toward the proximal end of the needle opposite the point; and
    b) a suture needle holder comprising:
        an elongated tube having a proximal end and a distal end and having an outer wall extending there between enclosing an internal cavity;
        the distal end having a rounded surface with an external groove of sufficient depth to retain a suture therein;
        a pair of wings adjacent the distal end, each wing being pivotable from within the tube at a first end and having a second end which is radially extensible, the second end of said wing having a blind hole for removably receiving said suture needle in said blind hole, said needle being aligned substantially parallel with said elongated tube;
        a control element mounted on the proximal end of the tube, operatively connected to said pair of wings for pivoting purposes; and
        the tube further including a flushing port mounted near the proximal end, said flushing port being in fluid communication with the distal end.

2. The surgical suturing tool of claim 1 wherein said wings are movably stored in a pair of mating recesses in the tube by said control element to simultaneously rotate the wings, the wings being rotatable inwardly into a closed position which does not extend beyond the outer wall of the tube and to an open position extending radially outwardly from the tube.

3. The surgical suturing tool of claim 2 wherein said control element is a rotatable knob centrally located at the proximal end of said tube.

4. The surgical suturing tool of claim 3 wherein said distal end comprises an end cap, said end cap being rounded and grooved for receiving said suture.

5. The surgical suturing tool of claim 4 wherein said grooved end cap lies adjacent the wings.

6. The surgical suturing tool of claim 2 where said suture needle holder further includes a handle mounted on the proximal end of the tube, said handle extending radially outward of the tube.

7. The surgical suturing tool of claim 1 wherein each of said wings carries a needle-suture combination wherein said suture is fixedly secured within said needle blind hole for fixedly securing said suture.

8. A method for surgically suturing a wound, comprising the steps of:
    fastening two swaged suture needles to blind holes in wings of a suture needle holder such that said needles will follow an essentially linear path of travel;
    attaching a suture to a blind hole along a side of each needle, said blind hole having a groove leading thereto, said groove oriented to lead the surgical suture out of a side surface of each suture needle at an angle downward toward a proximal end of each needle opposite the point of each needle;

placing the suture within a suture retaining groove;

tensioning the suture;

inserting the suture needle holder into a wound to be sutured;

extending the suture needle away from the suture needle holder;

withdrawing the suture needle holder outwardly such that the needle penetrates the tissue to be sutured by the suture needle;

disengaging the suture needle from the suture needle holder;

pulling the suture needle and suture through the tissue to be sutured substantially parallel to said needle holder;

removing the suture needle holder from the patient, and suturing the patient.

9. A surgical suturing tool as in claim 1, wherein said needle is straight and said groove is oriented to provide an angle of exit ranging between 1 and 20 degrees.

10. A method as in claim 8, wherein each said needle is straight and said groove is oriented to provide an angle of exit ranging between 1 and 20 degrees.

* * * * *